(12) United States Patent
Peet et al.

(10) Patent No.: US 6,313,161 B1
(45) Date of Patent: *Nov. 6, 2001

(54) 2,19-METHYLENEOXY AND 2,19-METHYLENETHIO BRIDGED STEROIDS AS AROMATASE, 19-HYDROXYLASE INHIBITORS AND METHODS OF THEIR USE IN THE TREATMENT OF ESTROGEN MEDIATED DISORDERS

(75) Inventors: Norton P. Peet, Cincinnati; J. O'Neal Johnston, Milford; Joseph P. Burkhart, West Chester, all of OH (US)

(73) Assignee: Merrell Pharmaceuticals Inc., Bridgewater, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 92 days.

This patent is subject to a terminal disclaimer.

(21) Appl. No.: 09/426,993

(22) Filed: Oct. 26, 1999

Related U.S. Application Data

(63) Continuation of application No. 09/204,694, filed on Dec. 3, 1998, now abandoned, which is a continuation of application No. 08/872,460, filed on Jun. 11, 1997, now abandoned, which is a continuation of application No. 08/566,769, filed on Dec. 4, 1995, now abandoned, which is a continuation of application No. 08/210,796, filed on Mar. 18, 1994, now Pat. No. 5,491,136, which is a continuation-in-part of application No. 08/049,786, filed on Apr. 19, 1993, now abandoned, which is a continuation-in-part of application No. 07/803,239, filed on Dec. 5, 1991, now abandoned, which is a division of application No. 07/674,640, filed on Mar. 25, 1991, now Pat. No. 5,099,037, which is a continuation-in-part of application No. 07/453,441, filed on Dec. 20, 1989, now abandoned.

(51) Int. Cl.$^7$ ............... A61K 31/352; A61K 31/382; C07D 311/78; C07D 311/94; C07D 335/04

(52) U.S. Cl. ............ 514/432; 514/453; 549/24; 549/382

(58) Field of Search ............ 549/24, 382; 514/432, 514/453

(56) References Cited

U.S. PATENT DOCUMENTS

| | | |
|---|---|---|
| 3,166,553 | 1/1965 | Counsell et al. |
| 3,627,756 | 12/1971 | Klimstra |
| 3,954,980 | 5/1976 | Barton et al. |
| 4,814,324 | 3/1989 | Borris et al. |

OTHER PUBLICATIONS

Caspi et al., *Chem Abs.*, 65, 763g (1966).
Wicha et al., *Tetrahedron*, 25, 3961 (1969).
Luthy et al., *Helv. Chim. Acta*, 58, 1120 (1975).
Kocovsky, *J. Org. Chem.*, 53, 5816 (1988).
Armas et al., *J. Chem. Soc. Perkin Trans. I*, 1989, 405.
Njar et al., *Heterocycles*, 28, 1051 (1989).

*Primary Examiner*—Joseph K. McKane
*Assistant Examiner*—Taofiq S. Solola
(74) *Attorney, Agent, or Firm*—Barbara F. Kurys; Lawrence L. Martin; Balaram Gupta

(57) ABSTRACT

The present invention is directed to a method of using a certain compounds which are 2,19-methyleneoxy or 2,19 methylenethio bridged steroids, and related steroidal compounds as inhibitors of the enzyme steroid aromatase, 19-hydroxylase and as treatment for various estrogen dependent/mediated disorders including hormonal dependent breast cancer.

14 Claims, No Drawings

2,19-METHYLENEOXY AND 2,19-METHYLENETHIO BRIDGED STEROIDS AS AROMATASE, 19-HYDROXYLASE INHIBITORS AND METHODS OF THEIR USE IN THE TREATMENT OF ESTROGEN MEDIATED DISORDERS

The present application is a continuation of application Ser. No. 09/204,694 filed Dec. 3, 1998 now abandoned; which is a continuation of application Ser. No. 08/872,460 filed Jun. 11, 1997 now abandoned; which is a continuation of application Ser. No. 08/566,769 filed Dec. 4, 1995 now abandoned; which is a continuation of application Ser. No. 08/210,796 filed Mar. 18, 1994 now U.S. Pat. No. 5,491,136; which is a continuation-in-part of application Ser. No. 08/049,786 filed Apr. 19, 1993 now abandoned; which is a continuation-in-part of application Ser. No. 07/803,239, filed Dec. 5, 1991 now abandoned; which is a division of application Ser. No. 07/674,640, filed Mar. 25, 1991 now U.S. Pat. No. 5,099,037; which is a continuation-in-part of application Ser. No. 07/453,441, filed Dec. 20, 1989 and now abandoned; all of which are herein incorporated by reference.

BACKGROUND OF THE INVENTION

The estrogen hormones, estrone and estradiol, are involved in many physiological processes. The formation of these steroids is regulated by a number of enzymes. The enzyme aromatase is the rate limiting enzyme in the non-reversible conversion of the androgen hormones, testosterone and androstenedione, to the estrogen hormones, estradiol and estrone. Compounds such as aromatase inhibitors may thus regulate or inhibit androgen to estrogen conversion, and have therapeutic utility in treating clinical conditions potentiated by the presence of estrogens.

19-Nordeoxycorticosterone (19-norDOC) is known to induce mineralocorticoid hypertension. In the biosynthetic formation of 19-norsteroids, such as 19-norDOC, the initial step is the adrenal hydroxylation of an appropriate steroid such as deoxycorticosterone (DOC). The inhibition of the biosynthetic formation of 19-norDOC by inhibition of 19-hydroxylation of DOC would thus serve to decrease the level of 19-norDOC present in the animal involved and reduce hypertensive effects attributable to the presence of this material.

SUMMARY OF THE INVENTION

The present invention is directed to 2,19-bridged steroidal aromatase and 19-hydroxylase inhibitor compounds, their related intermediates, a process for their preparation, and their use in the treatment of various estrogen dependent/mediated disorders. These compounds may be represented by the following formulas:

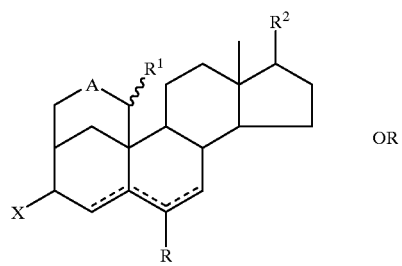

OR

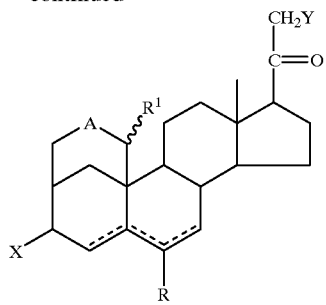

wherein

- - - - - represents a single or double bond,

A is O, S, SO, or $SO_2$,

R is H, $=CH_2$, $=O$, or $—OH$, $R^1$ is H or $C_{1-4}$ alkyl, $R^2$ is $=O$, $—OH$, or $—O—(C_{1-4}$ alkanoyl), X is $=O$, $=CH_2$, $—OH$, or $—O—(C_{1-4}$ alkanoyl), and Y is H, $—OH$, or $—O—(C_{1-4}$ alkanoyl), and when Y=H, OH, or $—O—(C_{1-4}$ alkanoyl), X may not include $—OH$, and R may not include $=O$ or $—OH$.

Examples of the alkyl groups referred to above are methyl, ethyl and propyl. Examples of the alkanoyl groups referred to above are acetyl, propionyl and butyryl. The double bonds, as represented by the dotted lines above are selected in such a way that the compounds must contain at least one double bond, usually in the A-ring of the standard steroid skeleton, although it can also be located at the 5,6-position in the B-ring. If the double bond is located at the 5,6-position, then the other dotted lines represent single bonds. When the system is doubly unsaturated, the double bonds are located at the 4,5- and the 6,7-positions.

Since the compounds of the present invention can be considered as containing a bridged steroid structure, it is possible to name them as derivatives of the basic steroid involved. When this is done with the oxygen-bridged compounds of the present invention, the compounds can be referred to as 2,19-(methyleneoxy) steroids. This indicates that a $—CH_2O—$ group connects the 2- and 19-positions with the carbon attached on the β-side of the 2-position and the oxygen attached to the 19-carbon atom. The sulfur bridged compounds can be described in a similar way.

DETAILED DESCRIPTION OF THE INVENTION

The compounds of the present invention are inhibitors of aromatase and 19-hydroxylase. As aromatase inhibitors, they are useful in treating hyperestrogenemia. The compounds are useful in controlling abnormally high levels of estrogens, both when the high levels observed are relatively steady, or when there are brief surges of elevated levels occurring as part of cyclical body functions. Both females and males can be treated, although obviously, the level of estrogens which would be considered high in males would be much lower than the amount considered high in females.

These compounds are also useful as anti-fertility agents to prevent ovulation or implantation in females, or to reduce the mating behavior in males where brain aromatization is required for such behavior. These compounds further have value in treating diseases of the male, such as gynecomastia, male infertility resulting from elevated estrogen levels, and hyperestrogenemia, which may precede myocardial infarction. Other male diseases for which the compounds of this invention are applicable include the therapeutic and/or prophylactic treatment of prostatic diseases, including prostatic hyperplasia, a disease of the estrogen dependent stromal tissue, and prostatic cancer.

There is substantial clinical evidence to indicate that many tumor types are associated with elevated estrogen production. Ovariectomy, adrenalectomy and hypophysectomy are commonly employed in patients with breast cancer as a means of reducing the amount of estrogen. Non-surgical procedures include treatments with high levels of steroids, anti-estrogens and inhibitors of steroidal enzymatic pathways. Treatment with antiestrogens results in about one-third of the patients obtaining objective tumor regressions. Andrenalectomy will cause regression of breast cancer in postmenopausal women with hormonal-dependent tumors, presumably as the result of reduction in available estrogen derived from androstenedione, whose source is primarily from the adrenals. Growth of several lines of breast cancer cells have been shown to be estrogen dependent or at least estrogen mediated, and can be inhibited, by compounds which antagonize estrogen action.

Breast tumors excised from postmenopausal women contain estradiol concentrations that are 5–50 fold higher than plasma estrogen levels. The aromatase activities of breast tumors are associated with stromal fibroblasts and adipose tissue. Fibroblast and adipose tissue aromatase activity is stimulated by a variety of promoters such as glucocorticoids, phorbal esters, cytokines and growth factors that can act through associated receptors via autocrine and paracrine pathways to promote tumor growth.

The aromatase inhibitors of the present invention can effectively prevent the biologically active estrogens from reaching endocrine tumors or reduce estrogen biosynthesis in those tumors capable of endogenous estrogen synthesis, thereby producing remissions of hormonal dependent breast cancer. Thus, these compounds are useful in the treatment of breast, ovarian, uterine and pancreatic tumors as well as disease condition such as galactorrhea, McCune-Albright syndrome, benign breast disease, endometriosis, and polycystic ovarian disease.

The bioconversion of deoxycorticosterone via a 19-hydroxylase pathway to 19-nordeoxycorticosterone potentiates its mineralocorticoid activity. Mineralocorticoid excess results in a syndrome characterized by hypokalemia, metabolic alkalosis, polydipsia, polyuria, and hypertensive conditions. Increased excretion of 19-nordeoxycorticosterone has been reported for hypertensive patients, including those with primary aldosteronism, Cushing's syndrome, 17β-hydroxylase deficiency, and individuals with essential hypertension. As 19-hydroxylase inhibitors, these compounds may be useful as antihypertensive agents and for management of edemous conditions often associated with sodium retention and potassium loss.

The compounds of the present invention which have a pregnane side chain are further useful in that a $C_{17-20}$ lyase enzyme can cleave the indicated side chain to give the corresponding 17-oxygenated androstene compounds which, as already indicated, are useful as aromatase inhibitors.

To achieve their desired effect, the compounds of the present invention may be administered orally, parenterally, for example, intravenously, intraperitoneally, intramuscularly, or subcutaneously, including the injection of the active ingredient directly into tissue or tumor sites, to a patient in need of treatment. The term patient is taken to mean a warm-blooded animal, for example, mammals such as humans, primates, cattle, dogs, cats, horses, sheep, mice, rats, and pigs. These compounds may also be administered in the form of a pharmaceutical preparation, and may further be incorporated into sustained delivery devices. The amount of compound administered will vary over a wide range and be any effective amount. Depending on the patient to be treated, the condition to be treated, and mode of administration, the effective amount of compound administered will vary from about 0.01 to 150 mg/kg of body weight per day, and preferably from about 0.1 to 50 mg/kg body weight per day.

For oral administration, the compounds can be formulated into solid or liquid preparations, such as capsules, pills, tablets, troches, powders, solutions, suspensions, or emulsions. The solid unit dosage forms can be a capsule which can be of the ordinary gelatin type containing the active compound and a carrier, for example, lubricants and inert filler such a lactose, sucrose and corn starch. In another embodiment, an active compound of the invention can be tableted with conventional tablet bases such as lactose, sucrose and corn starch in combination with binders such as acacia, corn starch, or gelatin, disintegrating agents such as potato starch, or alginic acids and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose and related sugar solutions, alcohols and glycols, such as propylene glycol or polyethylene glycol are preferred liquid carriers, particularly for injectable solutions.

The compounds can be administered in the form of a cutaneous patch, a depot injection, or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic®, silicone rubber manufactured by Dow Corning Corporation. Further information on suitable pharmaceutical carriers and formulation techniques are found in standard texts such as *Remington's Pharmaceutical Sciences*, Mack Publishing Company, Easton, Pa.

Inhibition of aromatase activity is demonstrated by using laboratory methods similar to procedures described in U.S. Pat. No. 4,322,416, and as published in Johnston et al., *Endocrinology* 115:776, 1984, and Burkhart et al., *Steroids* 45:357, 1985.

In this assay, the inhibitor is preincubated with enzyme prior to assaying for activity in the presence of high substrate levels. A time-related decrease in enzyme activity can be indicative of irreversible binding of the inhibitor with the enzyme.

In the time-dependent assay, an amount of the enzyme inhibitor in 100 μl of the assay buffer described above which will provide assay concentrations which are usually between 1 nM and 10 μM are added to 35 ml centrifuge tubes containing 600 μl of the NADPH generating system. The preincubation is started by the addition of 700 μl of aromatase preparation, usually 500–800 μg of microsomal protein per ml of assay buffer. These preparations are mixed using a vortex mixer and incubated for 0, 10, 20, or 40 minutes at 25° C. Then 100 μl of androstenedione (~6.8 μM) containing 1β-$^3$H androstenedione is added in assay buffer to provide an assay concentration of substrate (0.55 μM) which is at least ten times the $K_m$ of androstenedione (0.04 μM). Following vortexing, the enzyme incubation is continued for 10 minutes before being terminated by the addition of chloroform. The amount of radioactivity in the aqueous fraction is determined by scintillation procedures. The enzymatic activity for each concentration of inhibitor at each time period of preincubation is calculated as a percent of the "0" minute vehicle control arbitrarily set at 100%. Therefore, the present enzyme inhibition is expressed as a percentage: (100 percent minus percent enzyme activity with inhibitor present).

Enzyme kinetic analysis utilized Kitz-Wilson plots for time-dependent assays. These analyses provide estimates of apparent $K_i$ of inactivation which represents the inhibitor concentration required to produce half-maximal rate of enzyme inactivation. The pseudo first-order rate constant for enzyme inactivation ($k_{cat}$) and the half-time of inactivation (τ50) of infinite inhibitor concentrations were determined. The ratio of $k_{cat}/K_i$ (inactivation) provides an index number which increases with increased efficiency of enzyme inactivation and increased inhibitor affinity for the enzyme active site. When tested by this procedure, the following results were observed for compounds of this invention:

2,19-(methyleneoxy)androst-4-ene-3,17-dione, also named [3R-(3α,6aα,6bα,8aβ,11aα,11bβ)]-3,4,6b,7,8,8a,10,11,11a,11b, 12,13-dodecahydro-8a-methyl-6H-3,6a-methanocyclopenta-[5,6]naphth[1,2-c]oxocin-2,9-dione [Compound (4) below]: $K_i$ (nM)=17.6; $τ_{50}$ (min)=2.86; $k_{cat}/K_i$=227,300.

2,19-(methylenethio)androst-4-ene-3,17-dione, also named [3R-(3α,6aα,6bα,8aβ,11aα,11bβ)]-3,4,6b,7,8,8a,10,11,11a,11b, 12,13-dodecahydro-8a-methyl-6H-3,6a-methanocyclopenta-[5,6]naphtho[1,2-c]thiocin-2,9-dione [Example 3, last paragraph]: $K_i$ (nM)=53.0; $τ_{50}$ (min)=1.65; $k_{cat}/K_i$=132,103.

2,19-(methyleneoxy)androsta-4,6-diene-3,17-dione, also named [3R-(3α,6aα,6bα,8aβ,11aα,11bβ)]-3,4,6b,7,8,8a,10,11,11a,11b-decahydro-8a-methyl-6H-3,6a-methanocyclopenta [5,6]-naphth[1,2-c]oxocin-2,9-dione [Compound (15) below]: $K_i$ (nM)=21.6; $τ_{50}$ (min)=2.82; $k_{cat}/K_i$=189,658.

When assaying compounds for 19-hydroxylase inhibiting activity, compounds were solubilized in dimethyl sulfoxide (DMSO) at 10 mM and diluted in DMSO to provide 0.01–10 μM final concentration when 2 μL aliquots were added to microcentrifuge assay tubes. Assay buffer (10 mM KCl, 1 mM EDTA, 100 mM Tris-HCl at pH 8.0) which had been supplemented with an NADPH-generating system to provide assay concentrations of 1 mM NADPH, 3 mM glucose-6-phosphate and 1 I.U./ml glucose-6-phosphate dehydrogenase were incubated at 37° C. for 5 minutes prior to addition of hamster adrenal mitochondrial protein. Aliquots (180 μL) of this latter preparation containing 5.1 μg enzyme protein were assayed at 37° C for 5 minutes following the initiation of the assay by the addition of 20 μL of assay buffer containing radio-labeled DOC (0.85 μM final concentration, 0.01 μCi with 99.8% radiochemical purity, NEN Research Products, Boston, Mass.). Assays were quenched by the addition of 800 μL of 20% $CH_3CN$-2% HOAc. The reactants were centrifuged for 2 minutes at 15,000×g and analyzed by liquid chromatography (Beckman Instruments Inc., San Ramon, Calif.) on two $C_{18}$ Radial Pak columns (Waters, Millipore Corporation, Milford, Mass.) in series (5 μM particles, 0.8×10 cm each). Chromatographic buffer A was 10% $CH_3CN$-0.1% HOAC and buffer B was 80% $CH_3CN$-0.1% HOAC. The column was eluted at a flow rate of 1 ml/minute with a linear gradient from 0 to 30% buffer B over 36 minutes followed 100% buffer B. The amount of remaining labeled DOC substrate and initial hydroxylated products, corticosterone and 19-hydroxy-DOC, were separated and the radioactivity contained in each peak quantitated. The 19-hydroxylase activity was based on the quantity of radiolabeled DOC metabolized, since corticosterone and 19-hydroxy-DOC are the products of a single enzyme.

Unlabeled steroids were monitored by their absorbance at 240 nm with a Kratus Spectroflow 773 detector (Kratus Analytical Instruments, Ramsey, N.J.). The extinction coefficients for derivatives of DOC were assumed to be similar to that of DOC ($\epsilon$=17,200 $M^{-1}cm^{-1}$). Radioactivity of DOC metabolites was measured using an online Flow-One scintillation spectrometer (Radiomatic Instrument & Chemical Co., Inc., Tampa, Fla.) with a 1 ml flow cell.

Time-dependent enzyme inhibition was evaluated by preincubating the enzyme with steroidal compound for either 0 or 60 minutes at 37° C. prior to the addition of radiolabeled substrate for a 5 minute assay. Apparent $K_m$ for the first hydroxylation of DOC may be estimated by the double reciprocal plot of Lineweaver-Burk. $IC_{50}$'s may be graphically estimated from linear-log plots of enzyme activities and log of inhibitor concentrations.

According to the method of Johnston, J. O. et al., J. Steroid Biochem., 33:521, 1989, which is herein incorporated by reference, the compounds of the present invention were further evaluated for their effect upon intratumor aromatase activity. Table 1 graphically displays observed effects of 2,19-(methyleneoxy)-androst-4-ene-3,17-dione on intratumor aromatase synthesis. Compounds that exhibit time-dependent enzyme inhibition which can block intratumoral aromatase activity are preferred as potential therapeutic breast cancer agents.

TABLE 1

| Inhibition of Intratumor Aromatase Activity: Estrogen formed (picomoles/gram of tumor/hour) | | | | |
|---|---|---|---|---|
| | | Hours Post treament: -Absolute levels -% Inhibition | | |
| Method | Vehicle control | 2 | 4 | 6 |
| (3 mg/kg) | (absolute) | | | |
| intraveneous | 294 ± 5 | 88 ± 15 | 175 ± 12 | 186 ± 9 |
| | | 70 ± 5% | 41 ± 4% | 37 ± 3% |
| subcutaneous | 121 ± 85 | 68 ± 6 | 67 ± 3 | 78 ± 9 |
| | | 44 ± 5% | 45 ± 32% | 35 ± 7% |
| oral | 173 ± 9 | 49 ± 8 | 62 ± 7 | 64 ± 9 |
| | | 72 ± 5% | 64 ± 4% | 63 ± 5% |

The compounds of the present invention were also tested for the inhibition of tumor growth. Tumor growth inhibition was tested by the treatment of 50-day old female rats with the carcinogen, 7,12-dimethylbenz[a]anthracene [DMBA] and subsequently evaluated for tumor growth and/or remission (Huggins, C. et al., Nature 189:204, 1961; Russo, J. et al., Lab. Investigation 62: 244, 1990). Rats with DMBA-induced mammary tumors (≈3300–1300 mm³) were assigned to the following treatment groups: (1) Non-treated controls, (2) animals with subcutaneous implanted osmotic pump containing vehicle (DMSO/PEG$_{200}$, 1:4 v/v), and (3) 5 animals with subcutaneous implanted osmotic pump containing vehicle and 15 mg/kg/day of 2,19-(methyleneoxy)androst-4-ene-3,17-dione. Drug-treated animals also received 15 mg/kg/day via subcutaneous injections for the first two days of treatment as a priming dose. Tumor size was monitored for 42 days of drug treatment. Data are presented in Table 2 as the percent of animals which exhibited complete tumor regression, partial tumor regression (less than 50% of original tumor volume), no change (50 to 150% of original tumor volume) and tumor progression (greater than 150% of original tumor volume).

TABLE 2

DMBA Induced Mammary Tumor Growth

| | Response | | | |
|---|---|---|---|---|
| Treatment | Complete (0%) | Partial (<50%) | No change (50% ≦ x ≦ 150%) | Progressive (>150%) |
| Controls | 6.7 | 6.7 | 6.7 | 80.0 |
| 2,19-(methyleneoxy)-androst-4-ene-3,17-dione | 14.3 | 42.9 | 14.3 | 28.6 |

Various procedures can be used to prepare the compounds of the present invention. Scheme 1 below is used to prepare compound (4), 2,19-(methyleneoxy)androst-4-ene-3,17-dione. Alternatively, compound (4) may be named [3R-(3α, 6aα,6bα, 8aβ,11aα,11bβ)]3,4,6b,7,8,8a,10,11,11a,11b,12, 13-dodecahydro-8a-methyl-6H-3,6a-methanocyclopenta[5,6]naphth [1,2-c]oxocin-2,9-dione. To facilitate the understanding of the present invention, steroidal nomenclature and numbering are utilized in the procedures and examples that follow.

SCHEME 1

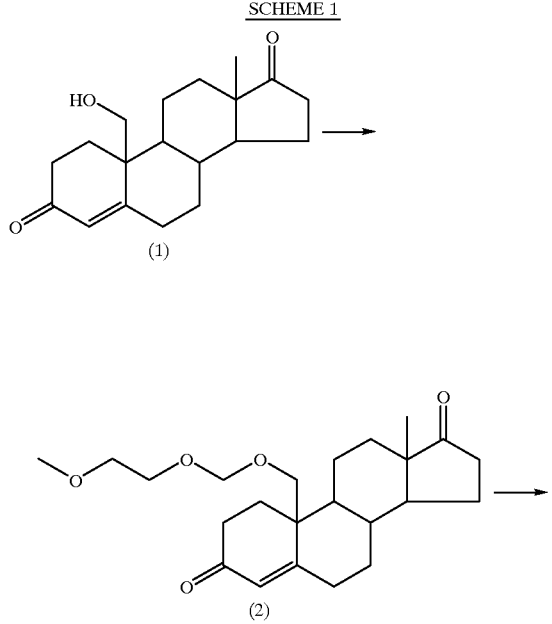

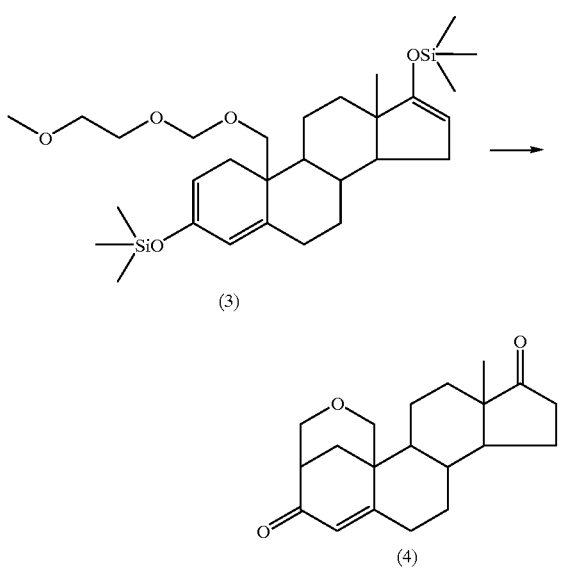

Commercially available steroid starting compound (1) reacted with diisopropylethylamine and 1-chloro-2,5-dioxahexane to form the compound, 19-[(2-methoxyethoxy)methoxy]androst-4-ene-3,17-dione (2). This compound is then reacted with a mixture of trimethylchlorosilane and lithium diisopropylamide to form the compound 19-[(2-methoxyethoxy)-methoxy]-3,17-bis[trimethylsilyl)oxy]-androst-2,4,16-triene (3). This compound is then treated with TiCl$_4$ to give the desired compound, 2,19-(methyleneoxy)androst-4-ene-3,17-dione (4). Alternatively, to prepare those compounds wherein A=S, the corresponding 19-mercapto steroidal starting compound is utilized, and the reaction proceeds analogous to Scheme 1. The compounds where A=SO and A=SO$_2$ are prepared from the corresponding compound where A=S by treatment with one or two equivalents of 3-chloroperoxybenzoic acid, respectively, in a solvent such as methylene chloride.

To prepare the compound bearing the hydroxyacetyl substituent at the 17-position (10), Scheme 2 is utilized:

SCHEME 2

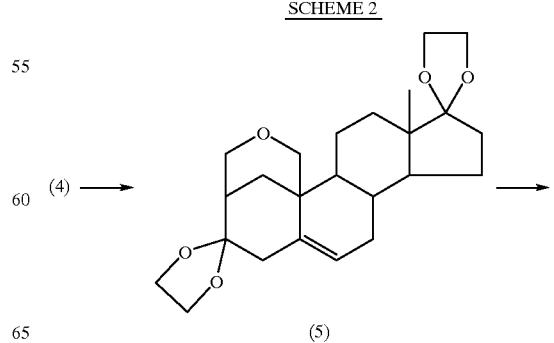

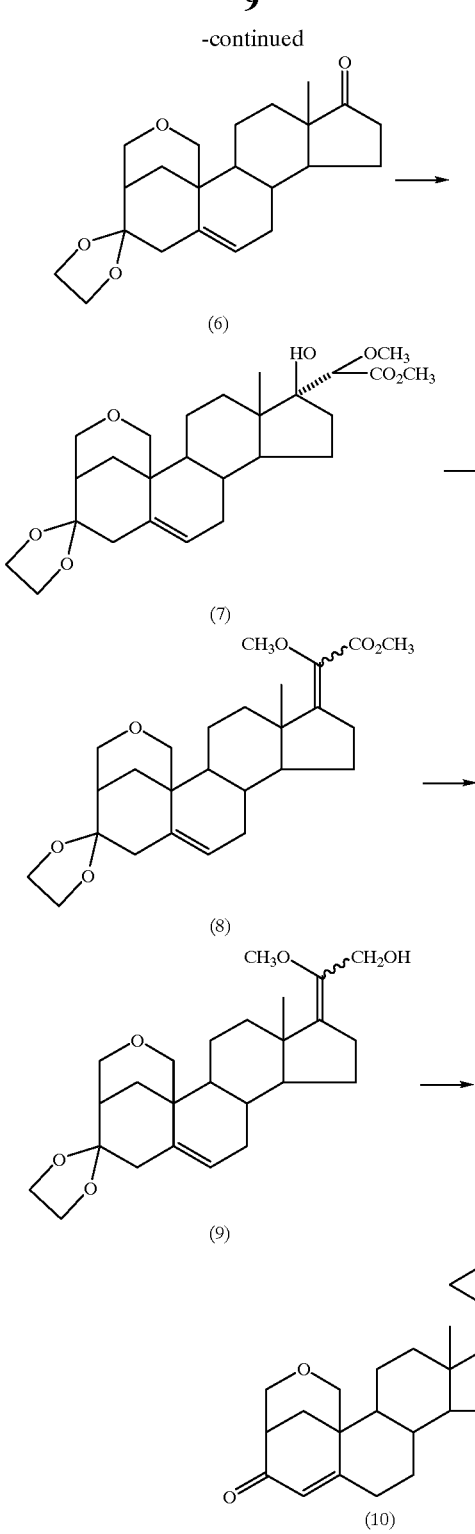

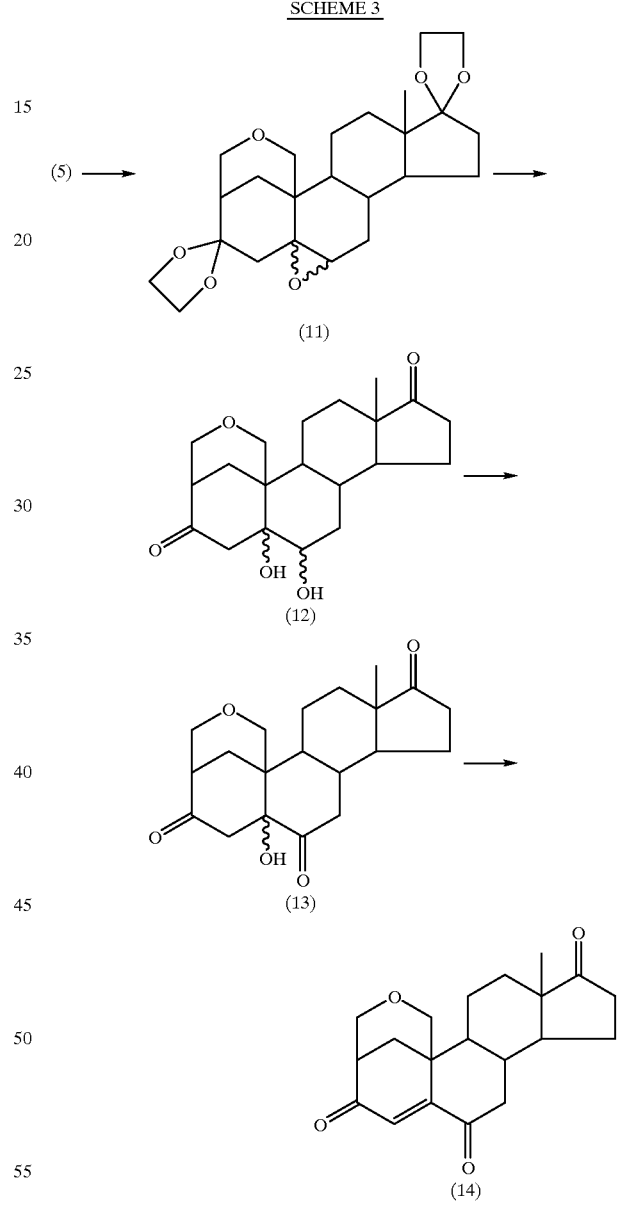

(i.e., the methylene group thereof), adds across the 17-ketone to give the 17-substituted 17-hydroxy steroid (7). Dehydration introduces a 17-exocyclic double bond. and the resulting methoxy ester (8) is reduced with a hydride reducing agent such as diisobutylaluminum hydride to give the corresponding alcohol (9), which is then further treated with acid to hydrolyze the enol ether and also the 3-ketal to give the desired 21-hydroxy-20-keto compound (10).

To prepare compound (14), 2,19-(methyleneoxy)androst-4-ene-3,6,17-trione, Scheme 3 is utilized:

The 2,19-(methyleneoxy)androst-4-ene-3,17-dione (4) is treated with a catalytic amount of acid such as methanesulfonic acid in an excess of ethylene glycol to form the corresponding 3,17-bis(ethylenedioxy) compound (5). This compound is then selectively hydrolyzed at the 17-position with 0.15% aqueous perchloric acid in t-butanol and dichloromethane to give the corresponding 17-ketone (6). The ketone is then reacted with methyl methoxyacetate and lithium diisopropylamide whereupon the indicated ester The diketal starting material (5) is treated with m-chloroperbenzoic acid in dichloromethane at 0° C. to produce the epoxide (11). The epoxide is opened to the corresponding diol (12) using perchloric acid in THF and H₂O The ketals are also removed in this process. The diol is then oxidized to the hydroxy-ketone by Jones oxidation. The hydroxy-ketone (13) is then taken up in benzene and dehydrated using p-toluenesulfonic acid to yield the steroidal trione (14).

Compounds containing multiple double bonds on the steroid ring system can be obtained by dehydrogenation of the appropriate starting compound. For example, dehydrogenation of 2,19-(methyleneoxy)androst-4-ene-3,17-dione (4) with chloranil in t-butanol gives the corresponding diene (15) as shown by Scheme 4 below.

SCHEME 4

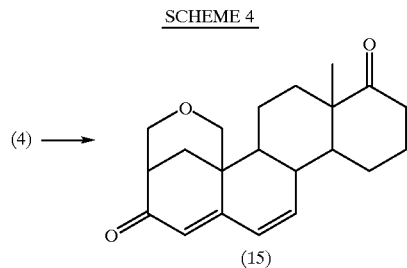

(4) →

(15)

To obtain compounds of the present invention wherein R is =CH$_2$, 2,19-(methyleneoxy)androst-4-ene-3,17-dione (4) is reacted with a formaldehyde acetal as shown by Scheme 5 below.

SCHEME 5

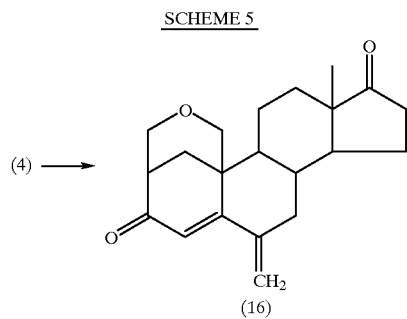

(4) →

(16)

Reagents such as p-toluenesulfonic acid, strong mineral acids, acidic ion exchange resin, or preferably, phosphoryl chloride with formaldehyde dimethyl or diethyl acetal, are most suitable to effect this condensation.

To obtain 2,19-(methyleneoxy)androst-4-ene-3,17-diol (17), Scheme 6 is utilized:

SCHEME 6

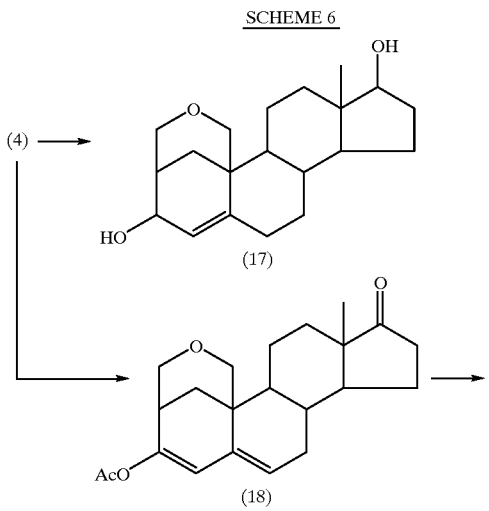

(4) →

(17)

(18)

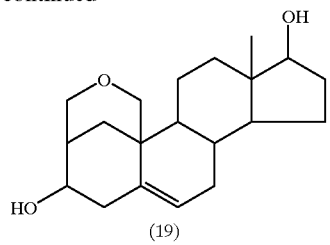

(19)

The starting compound, 2,19-(methyleneoxy)androst-4-ene-3,17-dione (4), is reduced with sodium borohydride in ethanol to yield the corresponding diol (17). To prepare the 5,6-ene diol (19), the starting compound, 2,19-(methyleneoxy)androst-4-ene-3,17-dione (4), is treated with a catalytic amount of p-toluenesulfonic acid and heating in a solvent such as Ac$_2$O. The mixture is then cooled. To this mixture is then added pyridine followed by ethanol to yield the dienol acetate (18).

Alternatively, the dienol acetate (18) may preferably be prepared by adding an excess of Ac$_2$O and a catalytic aimounl of 70% aqueous HClO$_4$ to the steroid (4) in EtOAc. The mixture is then stirred for 15 minutes and poured into dilute Na$_2$CO$_3$, extracted, and washed with dilute Na$_2$CO$_3$ and brine to yield the dienol acetate (18). The dienol acetate (18) is then treated with calcium borohydride in EtOH at −15° C. The reaction is quenched with HOAc and partitioned between EtOAc and H$_2$O to yield the diol (19). Treatment of the diol (19), with an anhydride, such as acetic anhydride, gives the corresponding diacetate.

In another approach to the preparation of the 5,6-ene diol (19), the steroid (4) is reacted with hexamethyldisila zane in pyridine solution and trimethylbromosilane to give 2,19-(methyleneoxy)-3,17-bis-(trimethylsilyloxy)androsta-3,5,16-triene which is then reduced with calcium borohydride in ethanol to give, after appropriate quenching, the desired product.

To prepare the compound wherein R$^1$ is CH$_3$, Scheme 7 is utilized.

SCHEME 7

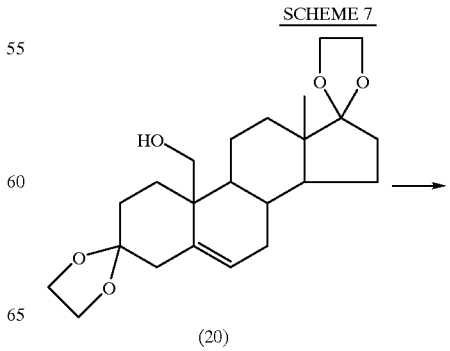

(20)

-continued

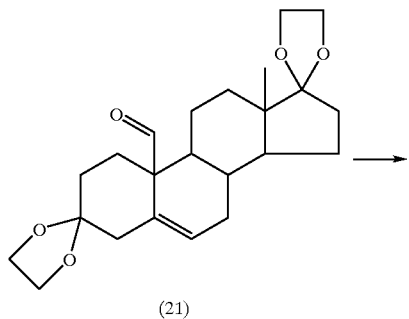

(21)

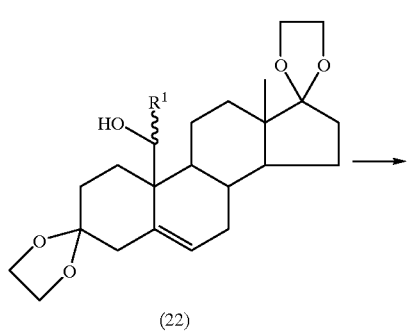

(22)

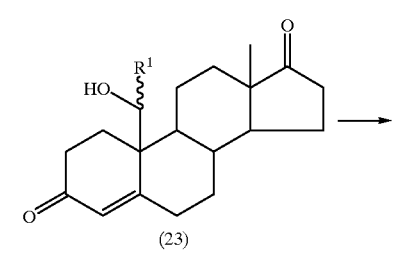

(23)

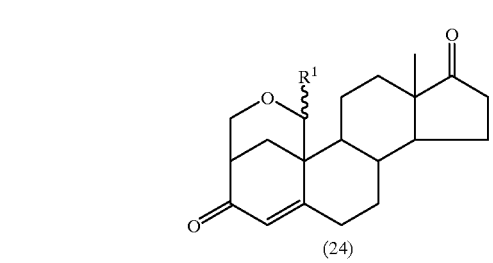

(24)

The known bisketal compound (20) undergoes a Swern oxidation to yield the oxidized bisketal (21). This compound is then treated with $R^1MgBr$ or $R^1Li$, wherein $R^1$ is defined above, to produce the $R^1$-substituted hydroxy compound (22). Treatment of (22) with aqueous HCl in THF yields the dione (23). Treatment of the dione (23) in a manner analogous to Scheme 1 yields the $R^1$-substituted 2,19-(methyleneoxy)-androst-4-ene-3,17-dione (24).

To prepare the compound wherein X is $=CH_2$, Scheme 8 is utilized.

SCHEME 8

(6) → 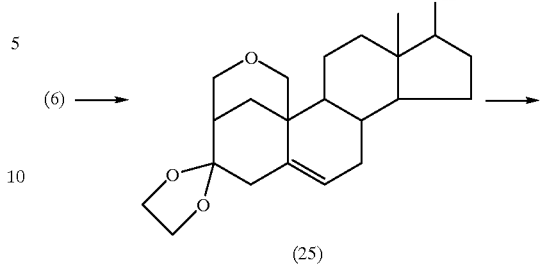

(25)

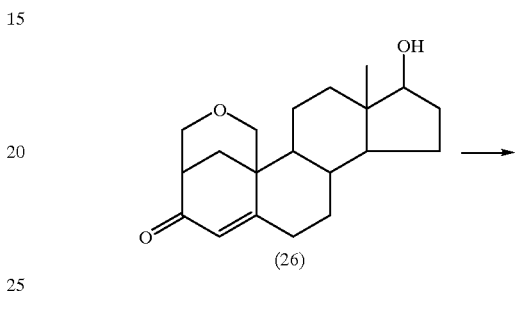

(26)

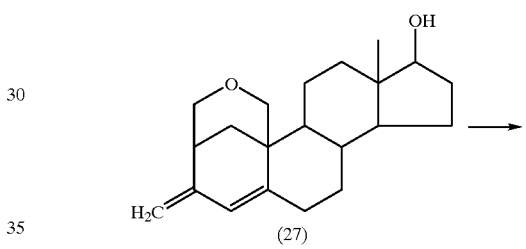

(27)

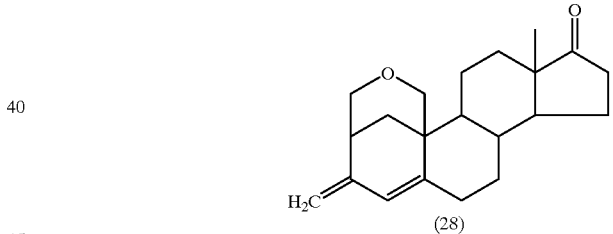

(28)

To the starting 17-keto compound (6), in EtOH, at. 0° C. is added an excess of $NaBH_4$. After 30 minutes, the reaction is quenched with $CH_3COCH_3$ and concentrated. The residue is added to $CH_2Cl_2$, washed with 0.5 N hydrochloric acid solution, water, then brine to yield the corresponding 17-hydroxy compound (25). To this compound (25) in THF is added aqueous hydrochloric acid solution to form the corresponding 3-keto-17-hydroxy compound (26). This compound (26) is then treated with $(C_6H_5)_3P=CH_2$ to yield the corresponding 3-methylene-17-hydroxy compound (27). This compound is then oxidized at C-17 by Jones oxidation to form the 3-methylene-17-keto compound (28). Optionally, compound (28) may then be treated in a manner analogous to Scheme 2 to form the corresponding 21-hydroxy-20-keto compound.

The following examples are provided to illustrate the present invention. They should not be construed as limiting it is any way.

EXAMPLE 1

To a stirred solution of 19-hydroxyandrost-4-ene-3,17-dione (1) (4.54 g, 15.0 mmol) in $CH_2Cl_2$ (40 ml) under argorn atmosphere was added diisopropylethylamine (5.23 ml, 30.0 mmol) followed by 1-chloro-2,5-dioxahexane (2.57 ml, 22.5 mmol). After 20 hours, the reaction was diluted with $CH_2Cl_2$ (60 ml) and the organics were washed with $H_2O$ (75 ml), 0.5 N hydrochloric acid (2×75 ml), saturated $NaHCO_3$ (35 ml), and brine (75 ml). Drying ($MgSO_4$) and concentration gave an orange oil (6.33 g). The oil was dissolved in 10 ml of EtOAc/hexane (65:35) and loaded onto a column. Flash chromatography (7.5×15 cm silica gel column), eluting with EtOAc/hexane (65:35) gave 19-[(2-methoxyethoxy)methoxy]-androst-4-ene-3,17-dione (2). (Weight: 4.44 g). HRMS calculated for $C_{23}H_{34}O_5$ (M+): 390.2406; found M+: 390.2401error=−1.3 ppm.

EXAMPLE 2

To a stirred solution of diisopropylamine (0.37 ml, 2.65 mmol) in THF (7 ml) under argon and cooled to −20° C. was added n-BuLi (1.03 ml, 2.42 M in hexane, 2.49 mmol). After 12 minutes, a cooled (−20° C.) solution of trimethylchlorosilane (0.74 ml, 5.81 mmol) in THF (1 ml) was added rapidly. After 2 minutes, a cooled (−20° C.) solution of the product of Example 1 (2) (324 mg, 0.83 mmol) in THF (2 ml) was added dropwise followed by a 0.5 ml THF rinse. The reaction was stirred at −20° C. for 30 minutes and then allowed to warm slowly to room temperature. The reaction was stirred at room temperature for 30 minutes, triethylamine (1 ml) was added and the reaction was diluted to a 50 ml volume with ethyl ether. The organics were washed with saturated $NaHCO_3$ (50 ml+20 ml) followed by brine/saturated $NaHCO_3$ (20 ml of a 3:1 mixture). Drying ($MgSO_4$) and concentration gave a pale yellow oil. To this product was added hexane, the mixture concentrated, and then placed under high vacuum for 5 minutes to remove any remaining THF and triethylamine, yielding 19-[(2-methoxyethoxy)methoxy]-3,17-bis-[(trimethylsilyl)oxy]androsta-2,4,16-triene (3) (quantitative).

EXAMPLE 3

To a stirred solution of the product of Example 2 (3) (0.83 mmol) in $CH_2Cl_2$ (8 ml) under argon and cooled to −20° C. was rapidly added a $TiCl_4$ solution (2.49 ml of a 1M $TiCl_4$ in $CH_2Cl_2$ solution, 2.49 mmol). A tan suspension resulted. Additional $CH_2Cl_2$ (8 ml) was added. The reaction suspension was stirred at −20° C. for 35 minutes, diluted with $CH_2Cl_2$ and poured into saturated $NaHCO_3$. The layers were separated and the aqueous layer was extracted with additional $CH_2Cl_2$. The combined organics were washed with saturated $NaHCO_3$ (2×), 0.5N hydrochloric acid (1×), followed by brine. Drying ($MgSO_4$) and concentration gave a milky oil. To this product was added 4 ml of EtOAc/hexane (50:50), the solid was crushed, and the suspension was heated with a heat gun and then allowed to cool to room temperature prior to loading the supernatant onto a flash column for chromatography (2×10 cm silica gel column). The supernatant was loaded as stated, eluted with EtOAc/hexane (50:50), and 15–20 ml fractions were collected. Concentration of the product containing fractions gave a pale yellow oil. $Et_2O$ was added to the residue and the flask was swirled to provide a solid. Concentration gave an oily, white solid (0.14 g). This product was then triturated with 2 ml of $Et_2O$/hexane (3:1). As much solid as possible was scraped from the side of the flask and the suspension was filtered to provide a white solid (56 mg). The solid was dried under high vacuum over refluxing acetone for 6 hours, yielding the compound of the formula below, mp 204–213° C. [3R-(3α,6aα,6bα,8aβ,11aα,-11bβ)]-3,4,6b,7,8,8a,10,11, 11a,11b,12,13-dodecahydro-8a-methyl-6H-3,6a-methanocyclopenta[5,6]naphth[1,2-c]oxocin-2,9-dione, or alternatively named, 2,19-(methyleneoxy)androst-4-ene-3,17-dione. (Weight remained 56 mg.).

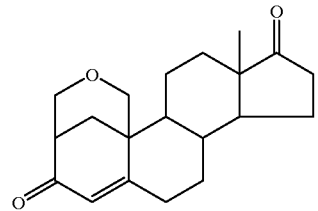

Elemental analysis: Calculated for $C_{20}H_{26}O_3$: C, 76.40; H, 8.34. Actual: C, 76.60; H, 8.53.

The corresponding sulfur compound, 2,19-(methylenethio) androst-4-ene-3,17-dione, was obtained in an analogous manner and melted at 183–199° C. This compound can also be named [3R-(3α,6aα,6bα,8aβ,11aα, 11bβ)]-3,4,6b,7,8,8a,10,11,11a,11b,12,13-dodecahydro-8a-methyl-6H-3,6a-methaneocyclopenta[5,6]naphtho[1,2-c] thiocin-2,9-dione.

EXAMPLE 4

The product of Example 3 was treated with a catalytic amount of methanesulfonic acid and an excess of ethylene glycol in solvent (benzene) and heated to reflux under Dean-Stark conditions to form the corresponding 3,17-bis (ethylenedioxy)-5-ene compound (5).

EXAMPLE 5

A solution of the product of Example 4 in dichloromethane and t-butanol was treated with 0.15% aqueous perchloric acid. The mixture was heated at gentle reflux for two hours with stirring and then allowed to cool to room temperature. The reaction mixture was then poured into saturated sodium carbonate solution and extracted into EtOAc. The EtOAc extract was washed with water and brine, dried over magnesium sulfate, concentrated, and chromatographed on silica gel eluting with EtOAc/hexane (2:3) to give the corresponding 17-one compound (6).

EXAMPLE 6

A solution of methyl methoxyacetate in tetrahydrofuran was slowly added to a cold solution of lithium diisopropylamide, prepared from diisopropylamine and n-butyl lithium in hexane, in the same solvent. A solution of the product of Example 5 in tetrahydrofuran was then added dropwise over 5–10 minutes and the solution is stirred for three hours at the same temperature. Saturated aqueous ammonium chloride solution was then added dropwise, and the mixture was poured into ice water and extracted with ethyl acetate. The extract was washed with brine, dried over sbdium sulfate, filtered, and concentrated to afford the 17-substituted steroid (7). The crude product was chromatographed on silica gel, eluting with 1:1 ethyl acetate:hexane to afford the product as a mixture of isomers.

EXAMPLE 7

A solution of the product of Example 6 in pyridine and $CH_2Cl_2$ was chilled to 0° C. and treated dropwise with thionyl chloride over 5–10 minutes. After stirring for 75 minutes at the same temperature, the solution was poured into ice water. The organic layer was washed twice with brine, dried over sodium sulfate, filtered and concentrated to afford crude product. Flash chromatography (30% ethyl acetate/70% hexane) afforded the methoxyester (8).

EXAMPLE 8

A solution of the product of Example 7 in toluene was chilled to −20° C. and treated dropwise with a 20% solution of diisobutylaluminum hydride in hexane. The solution was stirred at −20° C. for 30 minutes. Water was added and the mixture was stirred at 0° C. for 20 minutes, poured into ice water and extracted with 3:1 ether:dichloromethane. The exatracts were washed with brine, dried over sodium sulfate, and concentrated. The residue was subjected to flash chromatography eluting with 3:2 ethyl acetate:hexane to afford the alcohol (9).

EXAMPLE 9

To a solution of the product of Example 8 in THF was added 0.5 N aqueous HCl. After 4 days, the reaction was diluted with $CH_2Cl_2/H_2O$, the layers separated, and the organics washed with brine, dried over sodium sulfate, and concentrated. The hydroxyketone of the formula below was isolated by flash chromatography (silica gel) eluting with EtOAc/hexane (4:1). HRMS: Calcd for $C_{22}H_{31}O_4$: $MH^+$359.2222; Found: $MH^+$ 359.2204; Error: −5.0 ppm.

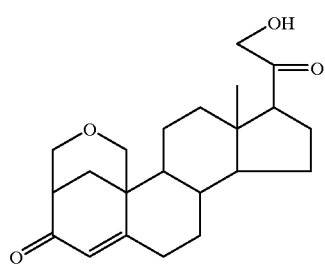

(10)

EXAMPLE 10

To a solution of the product of Example 4 (5) is added m-chloroperbenzoic acid in methylene chloride at 0° C. The mixture is maintained at 0° C. for 16 hours then diluted with methylene chloride and washed with water, 10% sodium carbonate, and brine, then dried and evaporated. Chromatography gives the epoxide (11).

EXAMPLE 11

To a solution of the product of Example 10 (11) in THF and water is added dropwise 70% aqueous perchloric acid and the reaction is stirred at room temperature for 48 hours. The mixture is diluted with methylene chloride, washed with aqueous $Na_2CO_3$ and brine, then dried ($MgSO_4$) and concentrated. Chromatography gives the corresponding diol (12).

EXAMPLE 12

To the product of Example 11 (12) in acetone at 0° C. is added dropwise Jones' reagent until a brown color persists for 15 minutes. The reaction is quenched with methanol. The mixture is then partitioned between methylene chloride and water. The organic phase is washed with brine, and then dried and concentrated. Chromatography gives the hydroxyketone (13).

EXAMPLE 13

To the product of Example 12 (13) dissolved in benzene is added a catalytic amount of p-toluenesulfonic acid. The mixture is heated at reflux for 30 minutes using a Dean-Stark water trap. The cooled solution is then poured into water. The organics are washed with aqueous $Na_2CO_3$ and brine, then dried and evaporated. The residue is chromatographed to afford the trione compound of the formula below, 2,19-(methyleneoxy)androst-4-ene-3,6,17-trione (14).

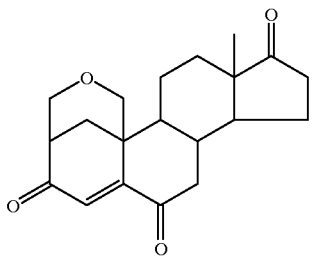

(14)

EXAMPLE 14

To the product of Example 3 (4) in t-butyl alcohol was added chloranil (2.25 equivalents). The mixture was refluxed for 3.5 hours, cooled and filtered and the filtrate concentrated. The residue was taken up in ethyl acetate and washed with water, aqueous NaOH, and brine. Drying and concentration, followed by chromatography afforded the compound [3R-(3α,6aα,6bα,8aβ,11aα,11bβ)]-3,4,6b,7,8, 8a,10,11,11a,11b-decahydro-8a-methyl-6H-3,6a-methanocyclopenta[5,6]naphth-[1,2-c]oxocin-2,9-dione of the formula;

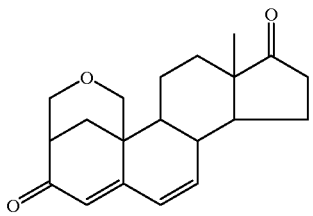

(15)

mp=193–197° C.

$^1H$ NMR($CDCl_3$); δ 6.32 (dd, 1H, vinyl), 6.22 (dd, 1H, vinyl), 6.04 (s, 1H, vinyl), 3.98 (ddd, 1H, ¼ $CH_2OCH_2$), 3.73 (dd, 1H, ¼ $CH_2OCH_2$), 3.64 (d, 1H, ¼ $CH_2OCH_2$), 3.55 (dd, 1H, ¼ $CH_2OCH_2$), 0.94 (s, 3H, 18—$CH_3$).

$^{13}C$ NMR($CDCl_3$): δ 219.0, 201.2, 157.8, 138.2, 128.5, 127.9, 69.7, 67.1, 49.1, 48.2, 47.8 44.2, 38.1 36.1, 35.5, 31.4, 21.3, 20.5, 13.6.

IR(KBr): 2956, 2854, 1740, 1662, 1616 $cm^1$.

EXAMPLE 15

A suspension of sodium acetate in absolute chloroform containing formaldehyde dimethyl acetal and phosphoryl chloride is stirred at reflux for 1 hour. After addition of the product of Example 3 (4), the mixture is treated dropwise with phosphoryl chloride over a period of 2.5 hours. The reaction is subsequently stirred at reflux for the appropriate time. The suspension is allowed to cool and under vigorous stirring a saturated aqueous solution of sodium carbonate is added dropwise until the pH of the aqueous layer becomes alkaline. The organic layer is separated, washed with water, and dried with sodium sulfate. After concentration and purification, the product obtained is the compound of the formula:

(16)

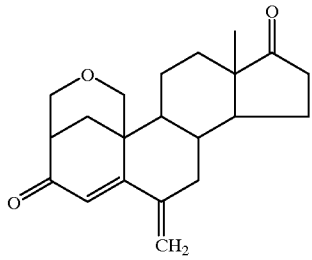

What is claimed is:

1. A method of treating benign prostatic hyperplasia which comprises administrating to a patient in need thereof an effective aromatase-inhibiting amount of a compound of the formula:

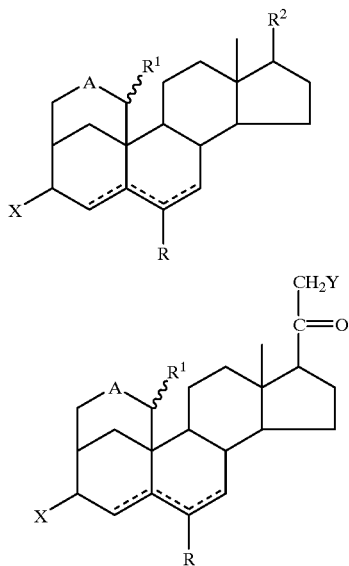

wherein:

----- represents a single or double bond, with the proviso that the compound must contain at least one double bond, A is O, S, SO, or $SO_2$, R is H, $=CH_2$, $=O$, or —OH, $R^1$ is H or $C_{1-4}$ alkyl, $R^2$ is $=O$, —OH, or —O—($C_{1-4}$ alkanoyl), X is $=O$, $=CH_2$, —OH, or —O—($C_{1-4}$ alkanoyl), and Y is H, —OH, or —O—($C_{1-4}$ alkanoyl), and when Y=H, —H, or —O—($C_{1-4}$ alkanoyl), X may not include —OH, and R may not include $=O$ or —OH.

2. A method according to claim 1 wherein the compound has the formula:

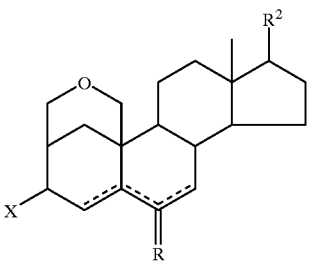

wherein:

----- represents a single or double bond, and X, R, and $R^2$ are defined as above.

3. A method according to claim 1 wherein the compound has the formula:

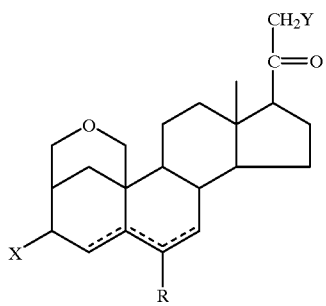

wherein:

----- represents a single or double boned bound; R, X, and Y are defined as above.

4. A method according to claim 1 wherein the compound is 2,19-(methyleneoxy)androst-4-ene-3,17-dione and is represented by the formula:

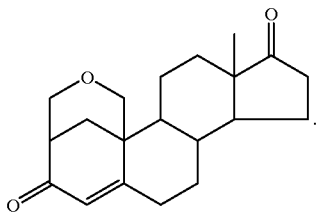

5. A method according to claim 1 wherein the compound is 2,19-(methylenethio)androst-4-ene-3,17-dione and is represented by the formula:

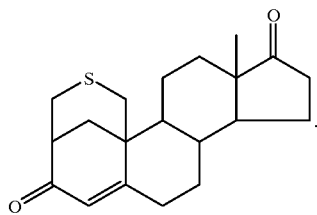

6. A method according to claim 1 wherein the compound is 2,9-(methyleneoxy)androsta-4,6-diene-3,17-dione and is represented by the formula:

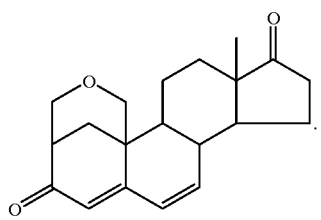

7. A method of inhibiting intratumoral aromatase of a breast cancer tumor which comprises administrating to a patient in need thereof an effective aromatase-inhibiting amount of a compound of the formula:

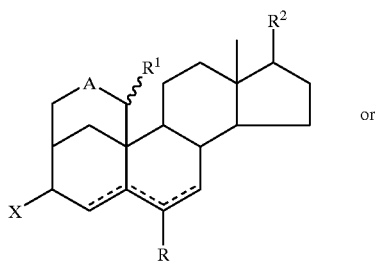

wherein:

----- represents a single or double bond, with the proviso that the compound must contain at least one double bond,
A is O, S, SO, or $SO_2$,
R is H, $=CH_2$, $=O$, or —OH,
$R^1$ is H or $C_{1-4}$ alkyl,
$R^2$ is $=O$, —OH, or —O—($C_{1-4}$ alkanoyl),
X is $=O$, $=CH_2$, —OH, or —O—($C_{1-4}$ alkanoyl), and
Y is H, —OH, or —O—($C_{1-4}$ alkanoyl), and when Y=H, —OH, or —O—($C_{1-4}$ alkanoyl), X may not include —OH, and R may not include $=O$ or —OH.

8. A method according to claim 7 wherein the compound has the formula:

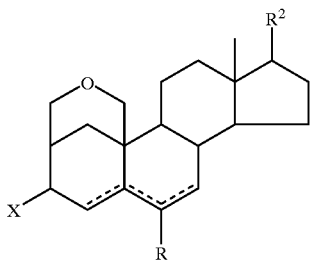

wherein:

----- represents a single or double bond, and X, R and $R^2$ are defined as above.

9. A method according to claim 7 wherein the compound has the formula:

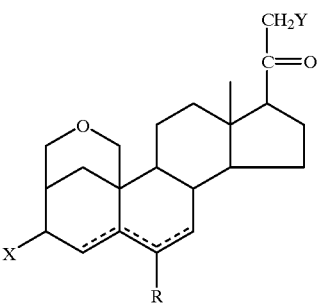

wherein:

----- represents a single or double bond, and R, X, and Y are defined as above.

10. A method according to claim 7 wherein the compound is 2-19-(methyleneoxy)-androst-4-ene-3,17-dione and is represented by the formula:

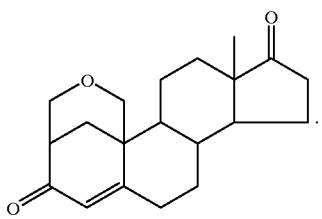

11. A method of treating a breast cancer tumor which results in growth inhibition or remission comprising administrating to a patient in need thereof an effective aromatase-inhibiting amount of a compound of the formula:

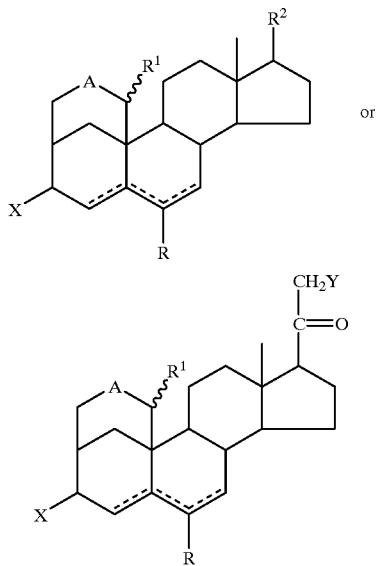

or

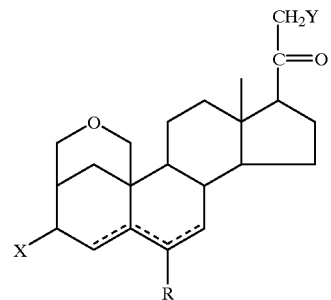

wherein:

----- represents a single or double bond, with the proviso that the compound must contain at least one double bond, A is O, S, SO, or $SO_2$, R is H, $=CH_2$, $=O$, or —OH, $R^1$ is H or $C_{1-4}$ alkyl, $R^2$ is $=O$, —OH, or —O—($C_{1-4}$ alkanoyl), X is $=O$, $=CH_2$, —OH, or —O—($C_{1-4}$ alkanoyl), and Y is H, —OH, or —O—($C_{1-4}$ alkanoyl), and when Y=H, —OH, or —O—($C_{1-4}$ alkanoyl), X may not include —OH, and R may not include $=O$ or —OH.

12. A method according to claim 11 wherein the compound has the formula:

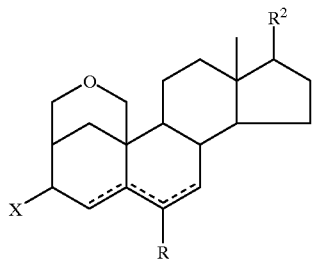

wherein:

----- represents a single or double bond, and X, R, and $R^2$ are defined as above.

13. A method according to claim 11 wherein the compound has the formula:

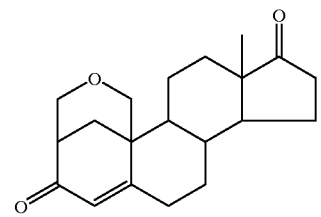

wherein:

----- represents a single or double bond; R, X, and Y are defined as above.

14. A method according to claim 12 wherein the compound is 2,19-(methyleneoxy)-androst-4-ene-3,17-dione and is represented by the formula:

* * * * *

UNITED STATES PATENT AND TRADEMARK OFFICE
CERTIFICATE OF CORRECTION

PATENT NO. : 6,313,161 B1
DATED : November 6, 2001
INVENTOR(S) : Peet et al.

Page 1 of 3

It is certified that error appears in the above-identified patent and that said Letters Patent is hereby corrected as shown below:

Column 3,
Line 42, reads "condition", and should read -- conditions --.

Column 5,
Line 28, reads "(τ50)", and should read -- ($\tau_{50}$) --.
Lines 35-37, reads "[3R-(3α,6aα,6bα,8aβ,11aα,11bβ)]-3,4,6b,7,8,8a,10,11,11a,11b, 12, 13-dodecahydro-8a-methyl-6H-3,6a-methanocyclopenta-[5,6]naphth[1,2-c]oxocin-2,9-dione" and should read -- [3R-(3α,6aα,6bα,8aβ,11aα,11bβ)]-3,4,6b,7,8,8a,10,11,11a,11b, 12,13-dodecahydro-8a-methyl-6H-3,6a-methanocyclopenta[5,6]naphth[1,2-c]oxocin-2,9-dione --.
Lines 41-43, reads "[3R-(3α,6aα,6bα,8aβ,11aα,11bβ)]-3,4,6b,7,8,8a,10,11,11a,11b,12,13-dodecahydro-8a-methyl-6H-3,6a-methanocyclopenta-[5,6]naphth[1,2-c]thiocin-2,9-dione" and should read -- [3R-(3α,6aα,6bα,8aβ,11aα,11bβ)]-3,4,6b,7,8,8a,10,11,11a,11b,12,13-dodecahydro-8a-methyl-6H-3,6a-methanocyclopenta [5,6]naphth[1,2-c]thiocin-2,9-dione --.
Lines 47-49, reads "[3R-(3α,6aα,6bα,8aβ,11aα,11bβ)]-3,4,6b,7,8,8a,10,11,11a,11b-decahydro-8a-methyl-6H-3,6a-methanocyclopenta [5,6]-naphth[1,2-c]oxocin-2,9-dione" and should read -- [3R-(3α,6aα,6bα,8aβ,11aα,11bβ)]-3,4,6b,7,8,8a,10,11,11a,11b-decahydro-8a-methyl-6H-3,6a– methanocyclopenta[5,6]naphth[1,2-c]oxocin-2,9-dione --.

Column 6,
Line 67, reads "189", and should read -- <u>189</u> --.

Column 7,
Line 1, reads "62:", and should read -- <u>62</u>: --.
Line 2, reads "(≈3300-1300 mm$^3$)", and should read -- (≈300-1300 mm$^3$) --.
Lines 35-38, reads "[3R-(3α,6aα,6bα,8aβ,11aα,11bβ)]-3,4,6b,7,8,8a,10,11,11a,11b, 12,13-dodecahydro-8a-methyl-6H-3,6a-methanocyclopenta[5,6]naphth[1,2-c]oxocin-2,9-dione" and should read -- [3R-(3α,6aα,6bα,8aβ,11aα,11bβ)]-3,4,6b,7,8,8a,10,11,11a,11b,12,13-dodecahydro-8a-methyl-6H-3,6a-methanocyclopenta[5,6]naphth[1,2-c]oxocin-2,9-dione --.

Column12,
Line 29, reads "aimounl", and should read -- amount --.

Column 14,
Line 63, reads "it is any way.", and should read -- it in any way.--.

UNITED STATES PATENT AND TRADEMARK OFFICE
CERTIFICATE OF CORRECTION

PATENT NO.    : 6,313,161 B1
DATED         : November 6, 2001
INVENTOR(S)   : Peet et al.

It is certified that error appears in the above-identified patent and that said Letters Patent is hereby corrected as shown below:

Column 16,
Lines 18-19, patent reads "2,19-(methylenethio) andros-4-ene-3,17-dione,",
and should read -- 2,19-(methylenethio)andros-4-ene-3,17-dione, --.
Line 57, reads "sbdium", and should read -- sodium --.

Column 18,
Line 54, reads "47.8 44.2", and should read -- 47.8, 44.2 --.

Column 19,
Line 64, reads "-H,", and should read -- -OH --.

Column 20,
Lines 1-10 reads,

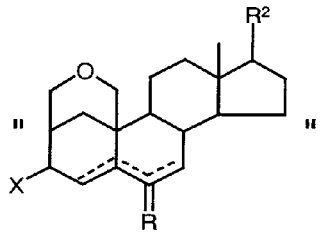

and shoud read

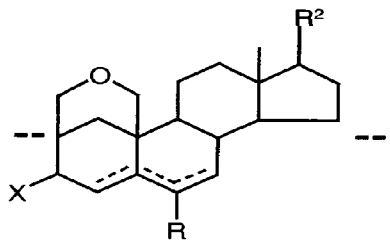

Column 21,
Line 13, reads "2,9-(methyleneoxy)androsta-4,6-diene-3,17-dione", and should read -- 2,19-(methyleneoxy)androsta-4,6-diene-3,17-dione --.

UNITED STATES PATENT AND TRADEMARK OFFICE
CERTIFICATE OF CORRECTION

PATENT NO. : 6,313,161 B1
DATED : November 6, 2001
INVENTOR(S) : Peet et al.

It is certified that error appears in the above-identified patent and that said Letters Patent is hereby corrected as shown below:

Column 22,
Line 48, reads "R,X,", and should read -- R, X, --.
Line 51, reads "2-19-(methyleneoxy)-androsta-4,6-diene-3,17-dione", and should read -- 2,19-(methyleneoxy)androsta-4,6-diene-3,17-dione --.

Column 24,
Line 36, reads "R,X,", and should read -- R, X, --.

Signed and Sealed this

Third Day of September, 2002

*Attest:*

*Attesting Officer*

JAMES E. ROGAN
*Director of the United States Patent and Trademark Office*